(12) United States Patent
Gindelberger

(10) Patent No.: US 11,242,330 B1
(45) Date of Patent: Feb. 8, 2022

(54) ORGANIC CATALYST AND METHOD FOR PREPARATION OF AROMATIC TRICYCLIC PYRANS

(71) Applicant: Acid Neutral Alkaline Laboratory, Longview, WA (US)

(72) Inventor: David Gindelberger, Ladue, MO (US)

(73) Assignee: Acid Neutral Alkaline Laboratory, Longview, WA (US)

( * ) Notice: Subject to any disclaimer, the term of this patent is extended or adjusted under 35 U.S.C. 154(b) by 0 days.

(21) Appl. No.: 17/221,618

(22) Filed: Apr. 2, 2021

Related U.S. Application Data

(60) Provisional application No. 63/153,437, filed on Feb. 25, 2021.

(51) Int. Cl.
*C07D 311/80* (2006.01)
*B01D 3/14* (2006.01)
*B01J 31/04* (2006.01)

(52) U.S. Cl.
CPC ............ *C07D 311/80* (2013.01); *B01D 3/143* (2013.01); *B01J 31/04* (2013.01); *B01J 2231/324* (2013.01)

(58) Field of Classification Search
CPC ........ C07D 311/80; B01D 3/143; B01J 31/04; B01J 2231/324
See application file for complete search history.

(56) References Cited

U.S. PATENT DOCUMENTS

| | | | |
|---|---|---|---|
| 8,222,292 | B2 | 7/2012 | Goskonda et al. |
| 9,345,771 | B2 | 5/2016 | Goskonda et al. |
| 9,630,941 | B2 | 4/2017 | Elsohly et al. |
| 10,596,124 | B2 | 3/2020 | Kaufman |
| 2004/0143126 | A1* | 7/2004 | Webster ............... C07D 311/80 549/390 |
| 2015/0057342 | A1 | 2/2015 | Koren et al. |
| 2017/0008868 | A1* | 1/2017 | Dialer ................. C07D 205/04 |
| 2018/0071210 | A1 | 3/2018 | Wilkhu et al. |
| 2021/0002247 | A1* | 1/2021 | Ham ..................... C07D 311/80 |

FOREIGN PATENT DOCUMENTS

| | | |
|---|---|---|
| CA | 2618705 C | 5/2007 |
| WO | 2012033478 A1 | 3/2012 |
| WO | 2015184127 A2 | 12/2015 |

OTHER PUBLICATIONS

Golombek et al. (Conversion of Cannabidiol (CBD) into Psychotropic Cannabinoids Including Tetrahydrocannabinol (THC): A Controversy in the Scientific Literature, Toxics, 8, 41, pp. 1-20, Published 2020) (Year: 2020).*

Hazekamp et al. (Comprehensive Natural Products II, 2010, 3.24.2.3 A Phytochemical Classification of Cannabinoids, pp. 1-12 (Year: 2010).*

Norris (So Long, CBD-Delta-8 Is the Latest THC Substitute That'll Help you Zen Out, 8 pages, Published 2020 (Year: 2020).*

* cited by examiner

*Primary Examiner* — Yevgeny Valenrod
*Assistant Examiner* — Blaine G Doletski
(74) *Attorney, Agent, or Firm* — Husch Blackwell LLP

(57) ABSTRACT

Provided herein are methods for converting CBD to a product mixture comprising $\Delta^8$-THC, $\Delta^9$-THC, or a combination thereof. The methods provided herein may comprise one or more of (1) a contacting step wherein a starting material comprising CBD, a carboxylic acid catalyst, and optionally a solvent are added to a reaction vessel, thereby forming a reaction mixture; (2) a conversion step wherein at least a portion of the CBD is converted to THC, thereby forming a product mixture; and (3) optionally, a separation step wherein at least a portion of the carboxylic acid catalyst is removed from the product mixture. In preferred embodiments, the methods utilize a carboxylic acid that is commonly used as a food additive and is generally recognized as safe for human consumption. The methods provided herein do not require the use of catalysts or other reagents that are hazardous to human health.

24 Claims, No Drawings

ORGANIC CATALYST AND METHOD FOR PREPARATION OF AROMATIC TRICYCLIC PYRANS

BACKGROUND

In recent years, there has been increasing interest in the medicinal properties of cannabinoids, which are a family of chemical compounds derived from the *cannabis* plant. For example, cannabidiol (CBD) has long been used as an antiepileptic medication, and the potential use of CBD to treat other neurological disorders is an area of active research. Likewise, while tetrahydrocannabinol (THC) is known as the principal psychoactive constituent of *cannabis*, recent research has identified potential uses of THC to treat a variety of diseases, including chronic pain, spasticity, and symptoms associated with multiple sclerosis and other neurological disorders.

More recently, research has indicated that different isomers of THC may provide different beneficial effects. For example, $\Delta^8$-THC is a double-bond isomer of $\Delta^9$-THC.

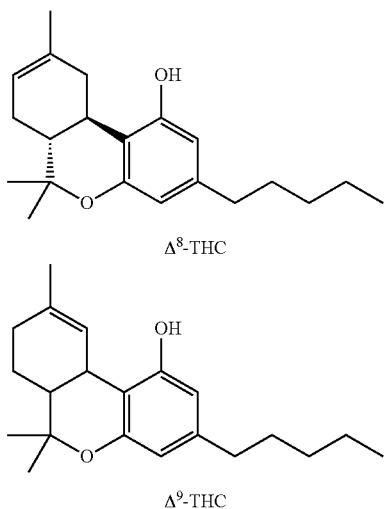

While both isomers are psychoactive, it is currently believed that $\Delta^8$-THC is less potent in this regard than $\Delta^9$-THC. Conversely, $\Delta^8$-THC is believed to be a more potent antiemetic agent than $\Delta^9$-THC.

Industrial hemp comprises CBD in an amount of about 2% by weight, which is significantly greater than either $\Delta^8$-THC (approximately 0.2% by weight) or $\Delta^9$-THC (approximately 0.1% by weight). Methods of converting CBD to $\Delta^8$-THC and $\Delta^9$-THC are therefore desirable. To date, however, a limited amount of research has been performed to identify such methods. For example, U.S. Pat. No. 7,399,872 to Webster et al. utilized a Lewis acid catalyst to promote the conversion of CBD to $\Delta^8$-THC and $\Delta^9$-THC. Unfortunately, the catalysts disclosed by Webster et al. (p-toluenesulfonic acid, boron trifluoride, and $BF_3Et_2O$) are all extremely hazardous to human health. This presents a safety hazard for persons who handle such materials, and also raises concerns about the presence of residual catalyst in the final products, which are intended for human consumption.

It is therefore desirable to develop new methods of efficiently converting CBD to $\Delta^8$-THC and $\Delta^9$-THC. Preferably, such methods would not require the use of catalysts or other reagents that are hazardous to human health. It is further desirable to develop methods that provide an improved degree of control over the relative proportion of $\Delta^8$-THC to $\Delta^9$-THC generated by the reaction.

SUMMARY

Provided herein are methods of converting CBD to THC. The methods provided herein may comprise one or more of (1) a contacting step wherein a starting material comprising CBD, a carboxylic acid catalyst, and optionally a solvent are added to a reaction vessel, thereby forming a reaction mixture; (2) a conversion step wherein at least a portion of the CBD is converted to THC, thereby forming a product mixture; and (3) a separation step wherein at least a portion of the catalyst is removed from the product mixture.

For example, provided herein is a method of converting CBD to THC, the method comprising contacting a starting material comprising CBD with a carboxylic acid catalyst, thereby forming a reaction mixture, and heating the reaction mixture to a temperature of at least about 60° C. for a period of at least about 30 minutes, thereby forming a product mixture comprising THC.

Also provided herein is method of converting CBD to THC, the method comprising (1) a contacting step, wherein a starting material comprising CBD is contacted with a carboxylic acid catalyst, thereby forming a reaction mixture; and (2) a conversion step, wherein CBD in the reaction mixture is converted to THC, thereby forming a product mixture comprising THC.

Also provided herein is a cannabinoid composition comprising THC, wherein the composition is produced by a method as provided herein.

Other objects and features will be in part apparent and in part pointed out hereinafter.

DETAILED DESCRIPTION

Provided herein are methods for converting CBD to a product mixture comprising THC. Preferably, the product mixture comprises $\Delta^8$-THC, $\Delta^9$-THC, or a combination thereof. The methods utilize carboxylic acids to catalyze the reaction. Carboxylic acids are weak acids, and generally pose less safety concerns than the strong acids utilized in the prior art (e.g., strong Bronstead or Lewis acids like mineral acids or boron trifluoride). In particular, the present methods can be carried out using carboxylic acids that are commonly used as a food additives and are generally recognized as safe for human consumption. Advantageously, the methods described herein do not require the use of catalysts or other reagents that are hazardous to human health.

Definitions

As used herein, CBD refers to cannabidiol.

As used herein, THC refers to tetrahydrocannabinol, and is inclusive of isomers including $\Delta^8$-THC and $\Delta^9$-THC.

As used herein, $\Delta^8$-THC refers to $\Delta^9$-tetrahydrocannabinol.

As used herein, $\Delta^9$-THC refers to $\Delta^9$-tetrahydrocannabinol.

As used herein, "carboxylic acid" refers to an organic acid that comprises at least one carboxyl group. Non-limiting examples of carboxylic acids include citric acid, acetic acid, maleic acid, ascorbic acid (for example, L-ascorbic acid, also known as Vitamin C), malic acid, tartaric acid, and lactic acid, the chemical structures of which are provided below.

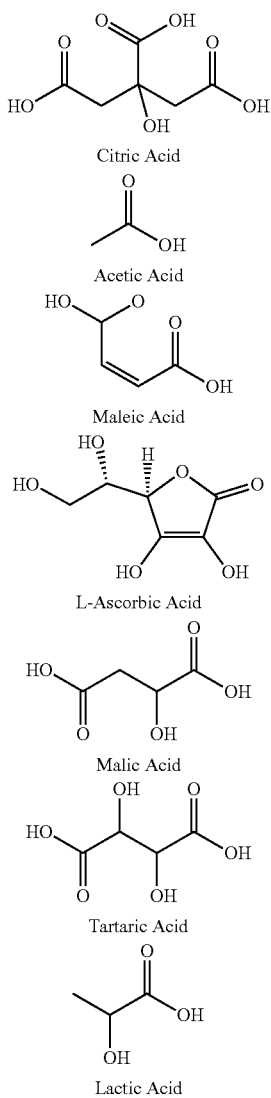

Citric Acid

Acetic Acid

Maleic Acid

L-Ascorbic Acid

Malic Acid

Tartaric Acid

Lactic Acid

Components

The methods provided herein may utilize one or more of (1) a starting material comprising CBD; (2) a carboxylic acid catalyst; and (3) optionally, a solvent. These components are described in further detail below.

Starting Material

The methods provided herein may utilize a starting material comprising CBD. The starting material may comprise, for example, *Cannabis* plant material (e.g., industrial hemp) or an extract thereof.

In preferred embodiments, the starting material comprises substantially pure CBD. For example, the starting material preferably comprises CBD in an amount of at least about 50%, at least about 60%, at least about 70%, at least about 80%, at least about 90%, or at least about 95% by weight.

The starting material may comprise, consist essentially of, or consist of a CBD distillate or CBD isolate. A particularly preferred starting material is CBD isolate.

Carboxylic Acid Catalyst

The methods provided herein utilize a carboxylic acid to catalyze the conversion of CBD to THC. Without being bound to a particular theory, it is currently believed that the carboxylic acid acts to catalyze the conversion of CBD to THC by cationic activation of the exocyclic olefin in CBD.

The carboxylic acid catalyst comprises one or more carboxylic acids. Non-limiting examples of suitable carboxylic acids include citric acid, acetic acid, maleic acid, ascorbic acid, malic acid, tartaric acid, and lactic acid. For example, the carboxylic acid catalyst may comprise citric acid.

If desired, the reaction may be catalyzed by a combination of two or more carboxylic acids. As a non-limiting example, the carboxylic acid catalyst may comprise citric acid and malic acid.

Solvent

The methods disclosed herein is enable the conversion of CBD to THC without the use of a solvent. In many cases, this represents a significant advantage; if desired, the reaction can be carried out using only two components (e.g., a starting material comprising CBD, and a carboxylic acid).

In some cases, however, the use of a solvent may be desirable. For example, a solvent may improve the ease of processing the product mixture, which can be difficult to work with due to the high viscosity of THC. In some cases, the final product is a dosage form that requires the presence of a solvent, and adding the solvent during the process described herein is therefore convenient. Additionally, and again without being bound to a particular theory, it is believed that the presence of a solvent may affect the relative amounts of minor cannabinoids (i.e., cannabinoids other than CBD or THC) produced during the conversion step. Non-limiting examples of suitable solvents include alcohols, alkanes, edible oils, and any other emulsifiers or surfactants approved for use in pharmaceutical formulations.

The solvent may comprise an alcohol. The alcohol may be, for example, a $C_1$ to $C_6$ organic alcohol. Non-limiting examples of suitable alcohols include methanol, ethanol, and isopropanol. A preferred solvent is isopropanol.

The solvent may comprise an alkane. The alkane may be, for example, a $C_1$ to $C_{10}$ alkane, more preferably a $C_5$ to $C_8$ alkane. Non-limiting examples of preferred alkanes include hexane and heptane.

The solvent may comprise an edible oil. For example, the solvent may comprise a vegetable oil. A preferred solvent is coconut oil. The use of an edible oil is particularly desirable were the desired final product is an edible formulation. In those cases, an edible oil (e.g., coconut oil) may be used as a solvent and simply carried through into the final, edible formulation.

The solvent may comprise one or more emulsifiers or surfactants approved for use in pharmaceutical formulations. Non-limiting examples of suitable emulsifiers and surfactants include ethoxylated fatty acid derivatives (e.g., polyoxyl stearate) and polysorbate-type nonionic surfactants. For example, the solvent may comprise polyoxyl stearate.

Reaction Procedure

The methods provided herein may comprise one or more of (1) a contacting step wherein a starting material comprising CBD, a carboxylic acid catalyst, and optionally a solvent are added to a reaction vessel, thereby forming a reaction mixture; (2) a conversion step wherein at least a portion of the CBD is converted to THC, thereby forming a product mixture; and (3) optionally, a separation step wherein at least a portion of the catalyst is removed from the product mixture. These steps are described in further detail below.

Contacting Step

The methods provided herein may comprise a contacting step wherein a starting material comprising CBD, a carboxylic acid catalyst, and optionally a solvent are added to a reaction vessel, thereby forming a reaction mixture.

The components may be added in any order. Preferably, the starting material is added first, followed by the catalyst, and optionally followed by the solvent.

Optionally the reaction mixture may be stirred (e.g., using a stir bar).

If a solvent is used, the reaction mixture may be heated in order to fully dissolve the CBD in the solvent. The reaction mixture may be heated, for example, to a temperature of at least about 30° C., at least about 40° C., at least about 50° C., or at least about 60° C. in order to dissolve the CBD. Typically, when a solvent is used, the reaction mixture is heated to a temperature of from about 30° C. to about 70° C., from about 40° C. to about 70° C., or from about 45° C. to about 65° C. in order to dissolve the CBD.

Typically, the reaction mixture comprises the starting material in an amount of at least about 50% by weight, for example, at least about 60%, at least about 70%, at least about 80%, at least about 90%, at least about 95%, at least about 96%, at least about 97%, at least about 98%, or even at least about 99% by weight. Correspondingly, the reaction mixture typically comprises CBD in an amount of at least about 80% by weight, for example, at least about 90%, at least about 95%, at least about 96%, at least about 97%, at least about 98%, or even at least about 99% by weight.

The reaction mixture may comprise the carboxylic acid catalyst in an amount of from about 0.1% by weight to about 20% by weight, for example, from about 0.1% by weight to about 15% by weight, from about 0.1% by weight to about 10% by weight, or from about 1% by weight to about 10% by weight. Typically, the reaction mixture comprises the catalyst in an amount of less than about 20% by weight, less than about 10% by weight, less than about 5% by weight, less than about 4% by weight, less than about 3% by weight, less than about 2% by weight, or even less than about 1% by weight. The reaction mixture may comprise the catalyst in an amount of at least about 0.01% by weight, at least about 0.05% by weight, at least about 0.1% by weight, at least about 0.5% by weight, at least about 1% by weight, or at least about 2% by weight.

The reaction mixture may comprise CBD and the carboxylic acid catalyst in a molar ratio of at least about 1:1, for example, at least about 2:1, at least about 4:1, at least about 5:1, at least about 6:1, at least about 10:1, at least about 20:1, at least about 50:1, at least about 100:1, at least about 150:1, or even at least about 200:1. For example, the reaction mixture may comprise CBD and the carboxylic acid catalyst in a molar ratio of from about 4:1 to about 200:1, such as from about 5:1 to about 100:1, or from about 8:1 to about 80:1.

Conversion Step

The methods provided herein may further comprise a conversion step wherein at least a portion the CBD starting material is converted to THC, thereby providing a product mixture comprising $\Delta^8$-THC, $\Delta^9$-THC, or a combination thereof.

The conversion step may comprise heating the reaction mixture. For example, the reaction mixture may be heated to a temperature of at least about 100° C., such as at least about 120° C., at least about 130° C., at least about 140° C., at least about 150° C., at least about 160° C., at least about 170° C., at least about 180° C., at least about 190° C., or at least about 200° C. Typically, the conversion step is carried out at a temperature of from about 140° C. to about 220° C., for example, from about 150° C. to about 200° C., or from about 150° C. to about 190° C.

The conversion step may comprise heating the reaction mixture for a period of at least about 30 minutes, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours. For example, the conversion step may comprise heating the reaction mixture for a period of from about 30 minutes to about 6 hours, from about 1 hour to about 6 hours, from about 2 hours to about 6 hours, from about 2.5 hours to about 6 hours, or from about 2.5 hours to about 5 hours.

Without being bound to a particular theory, it has been observed that at higher temperatures, the reaction proceeds more rapidly and produces a higher proportion of $\Delta^8$-THC in the product mixture. Higher temperatures may therefore be used to ensure rapid and complete conversion of CBD to $\Delta^8$-THC, if desired.

The conversion step may be carried out under ambient air. Alternatively, the conversion step may be carried out under an atmosphere comprised substantially of nitrogen. As a further alternative, the conversion step may be carried out under vacuum conditions.

Optionally, the progress of the reaction may be monitored by periodically taking samples of the liquid reaction mixture and analyzing them, for example using gas chromatography (GC). For example, the reaction may be monitored by collecting a sample of the reaction mixture every 30 to 60 minutes.

The conversion step may further comprise cooling the reaction mixture to halt the halt the conversion of CBD to THC. The reaction may be stopped by cooling the reaction mixture to a temperature, for example, of less than about 140° C., less than about 130° C., less than about 120° C., less than about 110° C., less than about 100° C., less than about 80° C., or less than about 60° C.

Product Mixture

The conversion step provides a product mixture that comprises $\Delta^8$-THC, $\Delta^9$-THC, or a mixture thereof. The product mixture may further comprise unreacted CBD, and optionally other cannabinoids (which may be referred to herein as minor cannabinoids).

In preferred embodiments of the methods provided herein, at least about 30% by weight of the CBD in the starting material is converted to THC. For example, in preferred embodiments at least about 40% by weight, at least about 50% by weight, at least about 60% by weight, at least about 70% by weight, at least about 80% by weight, or at least about 90% by weight of the CBD in the starting material is converted to THC.

The product mixture may comprise a mixture of $\Delta^8$-THC and $\Delta^9$-THC. In some embodiments, the ratio of $\Delta^8$-THC to $\Delta^9$-THC in the product mixture is approximately 1:1. For example, the ratio of $\Delta^8$-THC to $\Delta^9$-THC in the product mixture may range from about 20:1 to about 0.05:1, from about 10:1 to about 0.1:1, from about 4:1 to about 0.25:1, from about 3:1 to about 0.3:1, from about 2:1 to about 0.5:1, or from about 1.5:1 to about 0.75:1.

In some embodiments, $\Delta^9$-THC comprises a significant percentage of the total amount of THC in the product mixture. For example, $\Delta^9$-THC may comprise at least about 10%, at least about 20%, at least about 30%, at least about 35%, or at least about 40% of the total amount of THC in the product mixture.

In other embodiments, the product mixture may comprise $\Delta^8$-THC in significant excess relative to $\Delta^9$-THC. For example, the product mixture may comprise $\Delta^8$-THC in a ratio, relative to $\Delta^9$-THC, of at least about 2:1, at least about 3:1, at least about 4:1, at least about 5:1, at least about 10:1, at least about 15:1, or even at least about 20:1. In still further embodiment, the product mixture may comprise $\Delta^8$-THC in a ratio, relative to $\Delta^9$-THC, of at least about 50:1, at least about 100:1, at least about 200:1, at least about 300:1, at least about 400:1, at least about 420:1, at least about 440:1, at least about 460:1, at least about 480:1, or even at least about 500:1.

For example, in some embodiments, $\Delta^8$-THC comprises at least about 70%, at least about 80%, at least about 90%, at least about 95%, at least about 98%, or at least about 99% of the total amount of THC in the product mixture.

Separation Step

The methods provided herein may further comprise a separation step wherein at least a portion of the carboxylic acid catalyst is removed from the product mixture.

The separation step is optional. If the carboxylic acid catalyst is not filtered out, it will typically be present in a low concentration (typically less than 100 ppm) in the final, formulated product. This concentration is typically not harmful, and in some cases may even be desirable for its nutritional value. For example, citric acid and ascorbic acid (i.e., Vitamin C) are nutrients that support human health, and it may therefore be desirable to carry these carboxylic acids through into the final, formulated product.

If desired, however, the carboxylic acid catalyst may be separated from the reaction product. For example, the carboxylic acid catalyst may be removed by vacuum stripping of the reaction mixture. As a further example, the carboxylic acid catalyst may be removed by distillation. As a still further example, the carboxylic acid catalyst may be removed by washing the product mixture with an aqueous solution comprising a food-safe base. A non-limiting example of a food-safe base is sodium bicarbonate.

Cannabinoid Compositions

Also provided herein is a cannabinoid composition comprising THC, wherein the composition is produced by a method as described above.

For example, the cannabinoid composition may comprise a product mixture as described above. The composition may, for example, comprise $\Delta^8$-THC and/or $\Delta^9$-THC in any of the amounts, concentrations, or ratios as described above with respect to the product mixture.

EXAMPLES

The following non-limiting examples are provided to further illustrate the present disclosure.

General Reaction Procedure

The reaction procedure described below was used in each of the following examples, unless otherwise indicated. In general, the reaction converts CBD in the starting material to a mixture of $\Delta^8$-THC and $\Delta^9$-THC.

CBD isolate is placed in a reaction container and the carboxylic acid catalyst is added. Optionally, a solvent is added and the mixture warmed to above 60° C. The reaction is then run at a temperature between 150° C. and 200° C. The reaction is monitored by gas chromatography (GC), and when the target conversion of CBD to THC is achieved, the reaction is stopped by cooling to a temperature of less than about 60° C. by placing a container comprising the reaction mixture into a cool water bath.

Cannabinoids present in the reaction product were identified by gas GC retention time after having established the method with known standards. The ratio of $\Delta^9$-THC to $\Delta^8$-THC in the reaction product was observed to depend on temperature, time and catalyst charge. In some cases, small amounts of other minor cannabinoids were also produced.

In the examples described below, gas chromatography was carried out using a Varian 450-GC equipped with a standard polysiloxane capillary column, a flame ionization detector and a split/splitless injector. Samples were dissolved in a volatile solvent such as ethanol or acetone and injected in 1-2 μl volumes. Varian "Interactive Graphics" 6.9.3 software was used to integrate the FID data.

Example 1

One gram of CBD isolate and 1 ml of acetic acid were charged to a thick-walled glass tube with a stir bar and sealed with a threaded Teflon cap. The mixture was warmed to 150° C. for 4 hours. The cannabinoid content of the product mixture consisted of 56% CBD, 8% $\Delta^8$-THC and 36% $\Delta^9$-THC, with the remainder being minor cannabinoids.

Example 2

CBD isolate, 1.35 grams, and maleic acid, 35 mg, were charged to a glass vial with a stir bar and capped. The mixture was warmed to 160° C. for 4 hours. The cannabinoid content of the product mixture consisted of 49% CBD, 14% $\Delta^8$-THC and 33% $\Delta^9$-THC, with the remainder being minor cannabinoids.

Example 3

CBD isolate, 4 grams, and citric acid, 100 mg, were charged to a glass vial with a stir bar and a vacuum adapter attached. The mixture was warmed to 160° C. for 2 hours under vacuum. The cannabinoid content of the product mixture consisted of 43% CBD, 14% $\Delta^8$-THC and 38% $\Delta^9$-THC, with the remainder being minor cannabinoids.

Example 4

CBD isolate, 1.2 grams, coconut oil, 1.2 grams and citric acid, 58 mg, were charged to a glass vial with a stir bar and capped. The mixture was warmed to 160° C. for 4 hours under vacuum. The cannabinoid content of the product mixture consisted of 42% CBD, 16% $\Delta^8$-THC and 37% $\Delta^9$-THC, with the remainder being minor cannabinoids.

Example 5

CBD isolate, 1 gram, and citric acid, 10 mg as a 60% solution in ethanol, were charged to a glass vial with and a stir bar. The vial was capped and the mixture was warmed to 160° C. for two hours. The reaction was proceeding but slowly so it was warmed to 175° C. for 2 additional hours. The cannabinoid content of the product mixture consisted of 30% CBD, 21% $\Delta^8$-THC and 46% $\Delta^9$-THC, with the remainder being minor cannabinoids.

Example 6

CBD isolate, 1 gram, and stearic acid, 250 mg, were charged to a glass vial with 100 ul ethanol and a stir bar. The vial was capped and the mixture was warmed to 150° C. for two hours. No appreciable reaction was noticed to the mixture was warmed to 160° C. for 2 additional hours. The cannabinoid content of the product mixture consisted of 96% CBD, 2% $\Delta^8$-THC and 1% $\Delta^9$-THC, with the remainder being minor cannabinoids.

Example 7

CBD isolate, 1 gram, and benzoic acid, 250 mg, were charged to a glass vial with 100 ul ethanol and a stir bar. The vial was capped and the mixture was warmed to 150° C. for two hours. No appreciable reaction was noticed. The mixture was then warmed to 160° C. for two additional hours. The cannabinoid content of the product mixture consisted of 95% CBD, 1% $\Delta^8$-THC and 1% $\Delta^9$-THC, with the remainder being minor cannabinoids.

Example 8

CBD isolate, 1.8 grams, and ascorbic acid, 180 mg, were charged to a glass vial with a stir bar. The vial was capped and the mixture was warmed to 180° C. for one hour. The ascorbic acid darkened during the reaction but the oil remained light yellow. The cannabinoid content of the product mixture consisted of 85% CBD, <1% $\Delta^8$-THC and 12% $\Delta^9$-THC, with the remainder being minor cannabinoids.

Example 9

CBD isolate, 1.8 grams, and malic acid, 24 mg, were charged to a glass vial with a stir bar. The vial was capped and the mixture was warmed to 160° C. for four hours. The oil remained light yellow. The cannabinoid content of the product mixture consisted of 27% CBD, 37% $\Delta^8$-THC and 34% $\Delta^9$-THC, with the remainder being minor cannabinoids.

Example 10

CBD isolate, 1.6 grams, and tartaric acid, 55 mg, were charged to a glass vial with a stir bar. The vial was capped and the mixture was warmed to 160° C. for four hours. The oil remained a very light yellow. The cannabinoid content of the product mixture consisted of 57% CBD, 10% $\Delta^8$-THC and 32% $\Delta^9$-THC, with the remainder being minor cannabinoids.

Example 11

CBD isolate, 1.4 grams, and lactic acid, 54 mg, were charged to a glass vial with a stir bar. The vial was capped and the mixture was warmed to 160° C. for four hours. The oil turned orange. The cannabinoid content of the product mixture consisted of 85% CBD, 2% $\Delta^8$-THC and 12% $\Delta^9$-THC, with the remainder being minor cannabinoids.

Example 12

CBD isolate, 1.2 grams, and fumaric acid, 70 mg, were charged to a glass vial with a stir bar. The vial was capped and the mixture was warmed to 180° C. for one hour. The oil turned light orange. The cannabinoid content of the product mixture consisted of 98% CBD, <1% $\Delta^8$-THC and 1% $\Delta^9$-THC, with the remainder being minor cannabinoids.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A method of converting cannabidiol (CBD) to tetrahydrocannabinol (THC), the method comprising:
    (1) a contacting step, wherein a starting material comprising CBD is contacted with a carboxylic acid catalyst, thereby forming a reaction mixture; and
    (2) a conversion step comprising heating the reaction mixture to a temperature of at least about 130° C., wherein at least about 30% by weight of the CBD in the reaction mixture is converted to THC, thereby forming a product mixture comprising THC.

2. The method of claim 1 wherein the carboxylic acid catalyst comprises one or more carboxylic acids selected from the group consisting of citric acid, acetic acid, maleic acid, ascorbic acid, malic acid, tartaric acid, and lactic acid.

3. The method of claim 2 wherein the carboxylic acid catalyst comprises citric acid.

4. The method of claim 1 wherein the conversion step comprises stirring the reaction mixture.

5. The method of claim 1 wherein the starting material comprises CBD in an amount of at least about 50% by weight.

6. The method of claim 1 wherein the reaction mixture comprises CBD in an amount of at least about 50% by weight.

7. The method of claim 1 wherein the reaction mixture comprises the carboxylic acid catalyst in an amount of from about 0.1% by weight to about 20% by weight.

8. The method of claim 1 wherein the reaction mixture comprises CBD and the carboxylic acid catalyst in a molar ratio of at least about 1:1.

9. The method of claim 1 wherein the reaction mixture comprises CBD and the carboxylic acid catalyst in a molar ratio of from about 4:1 to about 200:1.

10. The method of claim 1 wherein at least about 70% by weight of the CBD in the starting material is converted to THC in the product mixture.

11. The method of claim 1 wherein the product mixture comprises $\Delta^8$-THC and $\Delta^9$-THC.

12. The method of claim 11 wherein the ratio of $\Delta^8$-THC to $\Delta^9$-THC in the product mixture is from about 4:1 to about 0.25:1.

13. The method of claim 11 wherein the ratio of $\Delta^8$-THC to $\Delta^9$-THC in the product mixture is at least about 420:1.

14. The method of claim 1 wherein at least about 10% of the total amount of THC in the product mixture is $\Delta^9$-THC.

15. The method of claim 1 wherein at least about 80% of the total amount of THC in the product mixture is $\Delta^8$-THC.

16. The method of claim 1 wherein the conversion step is conducted under
    (a) a vacuum; or
    (b) an atmosphere consisting essentially of nitrogen.

17. The method of claim 1 wherein the conversion of CBD to THC is monitored by (1) collecting one or more samples of the reaction mixture; and (2) analyzing the one or more samples using gas chromatography.

18. The method of claim 1 wherein the reaction mixture further comprises a solvent selected from the group consisting of alcohols, alkanes, edible oils, emulsifiers, and surfactants.

19. The method of claim 1 further comprising a separation step wherein at least a portion of the carboxylic acid catalyst is removed from the product mixture.

20. The method of claim 19 wherein at least a portion of the carboxylic acid catalyst is removed:
   (a) by vacuum stripping of the reaction mixture;
   (b) by distillation of the reaction mixture; or
   (c) by washing the product mixture with an aqueous solution comprising sodium bicarbonate.

21. A method of converting CBD to THC, the method comprising:
   contacting a starting material comprising CBD with a carboxylic acid catalyst, thereby forming a reaction mixture; and
   heating the reaction mixture to a temperature of at least about 130° C. for a period of at least about 30 minutes; thereby forming a product mixture comprising THC.

22. The method of claim 21 wherein the carboxylic acid catalyst comprises one or more carboxylic acids selected from the group consisting of citric acid, acetic acid, maleic acid, ascorbic acid, malic acid, tartaric acid, and lactic acid.

23. The method of claim 22 wherein the conversion step comprises heating the reaction mixture to a temperature of from about 140° C. to about 220° C.

24. The method of claim 22 wherein the conversion of CBD to THC is halted by cooling the reaction mixture to a temperature of less than about 100° C.

* * * * *